US 8,562,609 B2

(12) United States Patent
Schnieders et al.

(10) Patent No.: US 8,562,609 B2
(45) Date of Patent: Oct. 22, 2013

(54) MINIMALLY INVASIVE BONE BROACH

(75) Inventors: Barry Schnieders, Plymouth, IN (US); Michael C. Jones, North Webster, IN (US); David W. Daniels, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 883 days.

(21) Appl. No.: 12/638,558

(22) Filed: Dec. 15, 2009

(65) Prior Publication Data

US 2010/0094295 A1    Apr. 15, 2010

Related U.S. Application Data

(63) Continuation of application No. 10/879,553, filed on Jun. 29, 2004, now Pat. No. 7,632,273.

(51) Int. Cl.
 *A61B 17/00* (2006.01)
(52) U.S. Cl.
 USPC .......................................................... 606/79
(58) Field of Classification Search
 USPC ................................................... 606/79–85
 See application file for complete search history.

(56) References Cited

U.S. PATENT DOCUMENTS

| | | | |
|---|---|---|---|
| 4,738,256 A | 4/1988 | Freeman et al. | |
| 4,790,852 A | 12/1988 | Noiles | |
| 5,002,578 A | 3/1991 | Luman | |
| 5,006,121 A | 4/1991 | Hafeli | |
| 5,019,082 A | 5/1991 | Frey et al. | |
| 5,261,915 A | 11/1993 | Durlacher et al. | |
| 5,324,293 A | 6/1994 | Rehmann | |
| 5,342,363 A | 8/1994 | Richelsoph | |
| 5,342,366 A | 8/1994 | Whiteside et al. | |
| 5,403,320 A | 4/1995 | Luman et al. | |
| 5,496,323 A | 3/1996 | Dye | |
| 5,496,324 A * | 3/1996 | Barnes ............................ | 606/79 |
| 5,540,694 A * | 7/1996 | DeCarlo et al. ................ | 606/80 |
| 5,653,765 A | 8/1997 | McTighe et al. | |
| 5,665,091 A | 9/1997 | Noble et al. | |
| 5,704,940 A | 1/1998 | Garosi | |
| 5,800,437 A | 9/1998 | Gustilo et al. | |
| 5,931,841 A | 8/1999 | Ralph | |
| 6,015,408 A | 1/2000 | Pichon et al. | |
| 6,120,508 A | 9/2000 | Grunig et al. | |
| 6,723,129 B2 | 4/2004 | Dwyer et al. | |
| 6,932,821 B2 | 8/2005 | White | |
| 2003/0171756 A1* | 9/2003 | Fallin et al. ..................... | 606/80 |
| 2004/0092951 A1* | 5/2004 | Serra et al. ...................... | 606/96 |
| 2005/0113839 A1 | 5/2005 | Yoon et al. | |
| 2005/0203524 A1 | 9/2005 | Penenberg | |
| 2005/0234462 A1 | 10/2005 | Hershberger | |
| 2005/0234463 A1 | 10/2005 | Hershberger et al. | |

* cited by examiner

*Primary Examiner* — Mary Hoffman
(74) *Attorney, Agent, or Firm* — Maginot, Moore & Beck, LLP (57) ABSTRACT

A device for creating a cavity in a bone, said cavity having a cross-section which has a generally triangular profile having a first side generally parallel with an axis of the bone and a second side forming an acute angle with the first side, and contiguous with a pre-existing conical cavity, includes a shaft having a longitudinal axis and including a proximal portion and a distal portion, wherein the proximal portion has a larger cross section perpendicular to the longitudinal axis than the corresponding cross section of the distal portion, and a broach non-rotationally supported by the shaft and having a first cutting side supported at the acute angle relative to the longitudinal axis of the shaft, wherein the distal portion of the shaft is formed to include witness marks which when registered with an indicator after advancing the shaft facilitate selection of an appropriately sized prosthesis component.

16 Claims, 7 Drawing Sheets

MINIMALLY INVASIVE BONE BROACH

This application is a continuation of co-pending application Ser. No. 10/879,553, filed on Jun. 29, 2004 (now U.S. Pat. No. 7,632,273 issued Dec. 15, 2009), the disclosure of which is herein totally incorporated by reference in its entirety.

BACKGROUND AND SUMMARY

This invention relates to the field of artificial joint prostheses and, in particular, to an improved instrument for broaching a cavity in bone for receiving a prosthesis.

For implantation of prosthetic stems, such as hip stems, accurate preparation of the bone or intramedullary canal is important in order to guarantee good contact between the prosthesis stem and sleeve and the bone. The underlying concept behind precise preparation is that a precise bone envelope reduces the gaps between the stem and sleeve of the implant (i.e. prosthesis or prosthetic component) and the bone, thereby improving the initial and long-term bone ingrowth/fixation. The bone canal is presently prepared for implantation of a prosthetic stem by drilling and reaming a resected end of a bone, such as a femur, and then preparing an area adjacent the drilled hole to provide a seat for the prosthetic stem or a proximal sleeve coupled to the stem of a modular prosthetic system. A sleeve of modular prosthesis system is disclosed in U.S. Pat. No. 5,540,694, the disclosure of which is incorporated herein by this reference.

Preparation of the area adjacent the reamed intramedullary canal may be accomplished by broaching or by milling. Currently available broaches or rasps used for bone preparation have limitations. Some such broaches or rasps rely solely on the surgeon for guidance. Currently available broaches and rasps suffer from a tendency to be deflected by harder sections of bone so that they do not create a precise triangular cavity for receipt of the stem or sleeve of the prosthesis.

Thus, milling is currently the preferred method of bone preparation in many orthopaedic applications because it is a precise method of bone preparation. A limitation of milling systems today is that they are typically formed so that the drive shaft extends at an angle relative to the remainder of the frame from the end of the miller cutter machining the bone. A fairly large incision must be made to accommodate such milling assemblies. A typical incision for preparing a femur for a total prosthetic hip replacement using a standard triangle miller system is nine inches long. It is not uncommon for incisions as large as 12 inches to be used in a total hip replacement procedure. Efforts have been made to configure triangle miller systems to reduce the size of the incision required to accommodate a triangle miller during a prosthetic operation. However, to accommodate any miller, it is necessary to make an incision which may be undesirably large for cosmetic or other reasons.

In a hip replacement operation, initially, an incision large enough to expose the proximal end of the femur and to accommodate the instruments to be used in the operation is made in the upper thigh of the patient. Then, the neck of the femur is resected at the appropriate varus-valgus and anterior-posterior locations (typically determined using a template) with a resection instrument such as an oscillating saw. Then the femoral canal is opened up and the femoral cortex is reamed in preparation for receipt of the distal stem component of the prosthesis. Typically a stepped starter drill is utilized to generate an initial hole in the intramedullary canal. The stepped starter drill is positioned to open the trochanteric region to guard against varus positioning of the reamer and prosthesis. To further protect against varus positioning a box osteotome can be used to remove additional bone from the medial aspect of the greater trochanter.

Once the femoral canal has been appropriately opened, reaming begins utilizing a straight reamer. Distal reaming is done using a series of sequentially larger reamer diameters. The final straight reamer utilized should be ½ mm larger than the minor diameter of the selected femoral stem. The initial reamer is typically different from the rest in that it is an end cut reamer utilized to assist in canal finding, while the remaining reamers are blunt tipped side cutting reamers. The reamers are passed into the canal until a witness mark associated with the length of the stem component of the prosthesis to be utilized is adjacent the greater trochanter. The surgeon then works up progressively until cortical contact is made. Distal reaming is complete when the surgeon has reamed out to cortical bone in the shaft region.

The proximal or cone portion of the femoral metaphysis is then performed. Progressively larger cone reamers attached to an appropriately sized pilot stem are utilized to perform the cone portion of the femoral metaphysis. The cone reamer is advanced until an appropriate witness mark on the shaft is adjacent the greater trochanter. Successively larger cone reamers are used until cortical contact is achieved in the proximal femur.

Once cone reaming is completed calcar preparation is performed. Calcar preparation has been performed using triangular miller, broaches and reamers. When hand guided broaches or rasps or triangular millers are utilized for calcar prepartion, the initial incision must be fairly larger to accommodate these instruments. Following calcar preparation, a trial sleeve and trial implant are inserted into the proximal end of the femur. The trial sleeve is utilized to determine if anteversion or version must be changed in the prosthesis by performing trial reductions and adjusting the version and anteversion of the proximal trial component appropriately. Based on the trials, the final prosthesis components are selected assembled and inserted into the bone.

Since the oscillating saw used for neck resection and the straight reamers and conical reamers used for canal preparation are typically smaller than the instrument used for calcar preparation, the calcar preparation instrument often dictates the size of the incision required to perform the operation. When a patient undergoes total hip replacement (THR) it is common for the patient to stay in the hospital for one to two weeks. Rehabilitation therapy lasts months and many patients do not fully recover for years. Some patients never fully recover. This recovery process poses a substantial psychological and financial strain on THR patients. Many patients are in the latter years of their lives and this recovery period represents a significant portion of the remaining years. Current trends in joint replacement surgery suggest that smaller incision size can lead to faster recovery, improved quadriceps function and increased patient satisfaction.

When the calcar preparation is performed using a guided calcar broach, minimally invasive surgery can be performed. The disclosed broaching system is utilized for the calcar preparation in a hip prosthesis operation.

In view of the above, it would be desirable to have a calcar preparation instrument that can be utilized through a smaller incision during a surgical process.

According to one aspect of the disclosure, an apparatus is provided for creating a cavity in a bone, said cavity (i) having a cross section which has a generally triangular profile having a first side generally parallel with an axis of the bone and a second side forming an acute angle with the first side, and (ii) being contiguous with a pre-existing conical cavity in the bone. The apparatus comprises as shaft and a broach. The shaft has a longitudinal axis. The broach is mounted to the shaft and has a first cutting side mounted at the acute angle relative to the longitudinal axis of the shaft. The first cutting side is formed to include teeth. The shaft and broach are configured so that when the longitudinal axis of the shaft is advanced into the bone along the axis of the bone, the teeth of the broach form the triangular cavity.

According to a second aspect of the disclosure an apparatus for creating a cavity in a bone for receiving a prosthesis which has a conical portion and a projection of a generally triangular profile is provided. The apparatus comprises a shell, a shaft and a broach. The shell comprises a conical portion which defines a longitudinal axis and a shaft-receiving cavity for receiving a shaft. The shaft is configured to be received in the shaft-receiving cavity and be movable with respect to the shell along the longitudinal axis when so received. The shaft is configured to carry a broach having a cutting surface disposed at an acute angle relative to the longitudinal axis. The broach has a generally triangular profile and includes oppositely facing spaced apart triangular shaped side walls between which the cutting surface extends. The broach is mounted to the shaft.

According to yet another aspect of the disclosure, a method for cutting a triangular cavity in bone is provided. The method comprises a providing a shaft step, an incising step and a cutting step. The provided shaft is configured to be movable relative to the bone to be prepared and includes a broach coupled thereto to dispose a cutting surface of the broach at an acute angle relative to the shaft. The shaft and broach have a width defined by the distance between the shaft and the outer most portion of the cutting surface. The incising step includes incising the patient adjacent the bone to be prepared to form an incision having a length approximating the width of shaft and broach. The cutting step includes cutting the cavity by driving the broach by moving the shaft relative to the bone.

The disclosed broaching system is configured to reduce the size of incision required for preparation of a bone to receive a prosthetic stem therein.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

The illustrative devices will be described hereinafter with reference to the attached drawings which are given as non-limiting examples only, in which.

Corresponding reference characters indicate corresponding parts throughout the several views. Like reference characters tend to indicate like parts throughout the several views.

DETAILED DESCRIPTION OF THE INVENTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The disclosed broaching system 10 allows a surgeon to prepare bone for receipt of an implant through a smaller incision 12 compared to existing surgical instruments. In the illustrated embodiment, the incision 12 has a width 13. Illustratively, the disclosed broaching system 10 can be utilized with an incision having a width 13 of less than two and a half inches. In one preferred embodiment, the width 13 of the incision 12 is two inches. The disclosed broaching system 10 is typically used for broaching of a triangular space 14 in a bone 16 adjacent the intramedullary canal 18 to facilitate receipt of a sleeve of a prosthesis that fits accurately in the intramedullary canal 18, distributes loads evenly and provides rotational stability to the prosthesis.

The disclosed broaching system 10 is particularly useful for preparing a bone 16 for receipt of a modular prosthesis having a plurality of stem components, a plurality of sleeves and a plurality of body components that may be assembled to provide a prosthesis appropriately sized and configured for a patient's specific anatomy. The disclosed broaching system 10 includes a plurality of broach shells 26, a plurality of pilot stems 42, and a plurality of guided broaches 20. In one illustrated embodiment, the plurality of guided broaches 20 comprises a single driver component 24 configured for mounting to any one of a plurality of broach tools 22.

Figure 2:
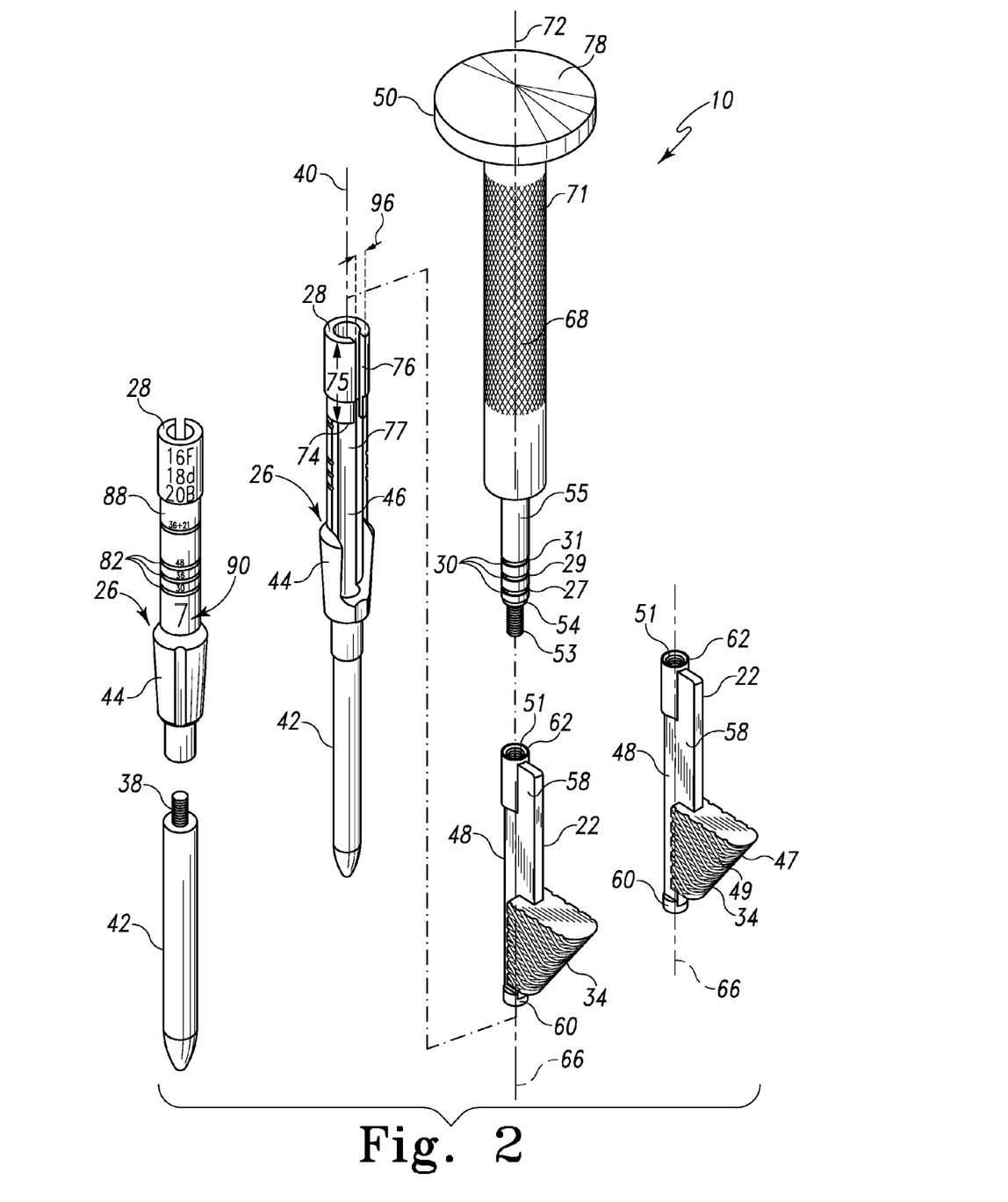
FIG. 2 is an exploded view of the broaching system of FIG. 1 showing the guided broach with the driver component disassembled from the broach tool, two broach tools intended to represent a plurality of broach tools each configured to be coupled to the driver component, two shells intended to represent a plurality of shells each configured to slidably receive a broach tool and two pilot stems each configured to mount to each shell.
Figure 3:
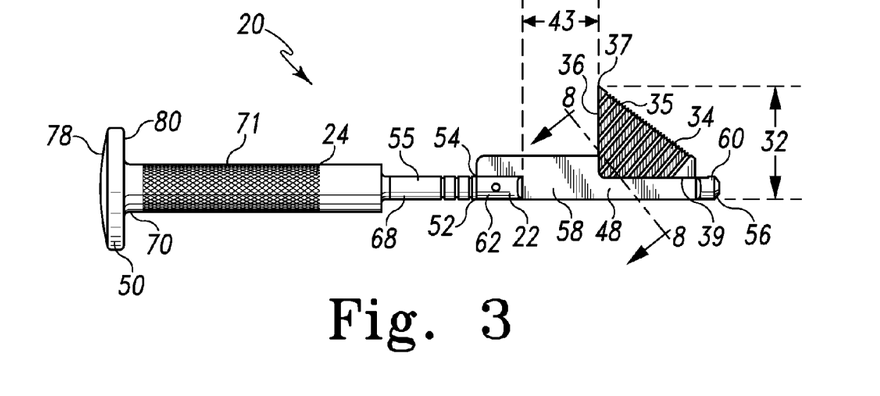
FIG. 3 is an elevation view of the guided broach of FIG. 1.
Figure 4:
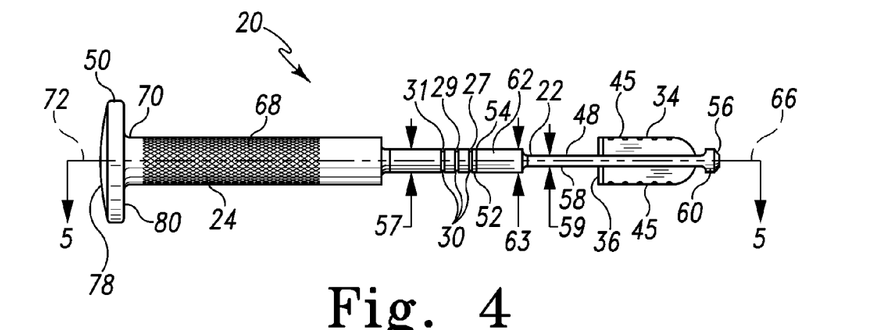
FIG. 4 is a plan view of the guided broach of FIG. 3.

With reference now to the drawings, wherein like reference characters designate like or corresponding parts throughout the several views, there is shown in FIG. 2 an exploded view of selected components of a broaching system 10 constructed in accordance with the invention. Broaching system 10 includes the plurality of guided broaches 20 for cutting the desired triangular-shaped cavity 14, the plurality of broach shells 26 for registering the broaching system 10 with a preexisting conical cavity in the patient's bone 16, and the plurality of pilot stems 42 configured to be attached a broach shell 26 for insertion in a prepared medullary canal 18 of the patient's bone 16. Indicators 28, 30 are provided for indicating the longitudinal location of guided broach 20 relative to the broach shell 26. In the embodiment illustrated in FIG. 2, the plurality of guided broaches 20 comprises a single driver component 24 configured to be removably coupled to any one of the plurality of broach tools 22. Those skilled in the art will recognize that a plurality of integrally formed driver components 24 and broach tools 22 could be provided as a plurality of guided broaches 20 within the scope of the disclosure. Providing a plurality of integrally formed guided broaches 20 makes it easier for instruments to be selected during the surgical procedure.

While in the illustrated embodiment, only two broach shells 26, two pilot stems 42, and two broach tools 22 are shown, it is to be understood that a plurality of broach shells 26, pilot stems 42 and broach tools 22 may be made available to the surgeon using the disclosed broaching system 10. Each broach tool 22 is configured to be coupled to the driver component 24. Thus a plurality of guided broaches 20 may be formed each utilizing the same driver component 24. Each broach shell 26 is configured to slidably receive a portion of the broach tool 22 and act as a guide therefore during calcar preparation of the bone 16. Each pilot stem 42 is configured to mount to each broach shell 26 to facilitate stable seating of the broach shell 26 and pilot stem 42 in the prepared bone 16. Thus, the appropriate instrumentation for broaching the triangular cavity 14 can be selected and assembled by a surgeon to form a broach assembly 19 during a prosthetic operation.

Figure 1:
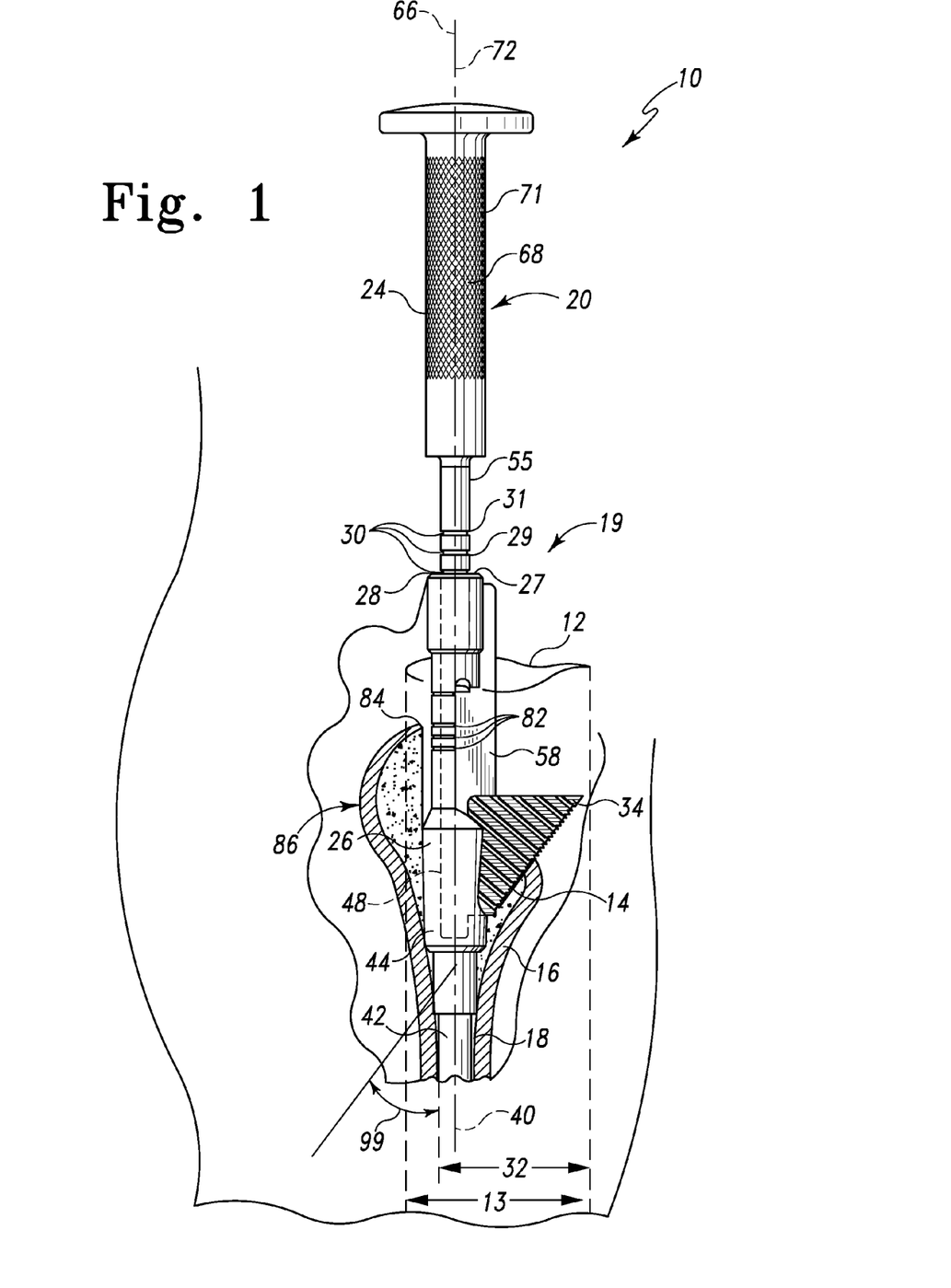
FIG. 1 is a view with parts broken away of a broach assembly formed form components of a broaching system inserted through an incision into a resected femur of a patient using a selected broach shell and pilot stem and a selected guided broach received in the selected broach shell.

As shown, for example in FIGS. 1 and 2, broach shell 26 has a longitudinal axis 40. Pilot stem 42 is removably attached to the main body of the broach shell 26 by, for example, a threaded shaft 38 extending from the proximal end of the pilot stem 42 which is configured to be received in a threaded cavity in the distal end of the broach shell 26. The broach shell 26 also has an external frustoconical surface 44 which engages the wall of the pre-existing conical cavity, as shown, for example, in FIG. 1. In addition, the broach shell 26 has shaft-receiving cavity 46 formed concentrically about the longitudinal axis 40 for receiving the stem component or shaft 48 of the broach tool 22 and allowing the longitudinal axis 66 of the shaft 48 of the broach tool 22 to move along longitudinal axis 40. In the illustrated embodiment, shaft-receiving cavity 46 is an internal guide surface defining a cylindrical cavity or passage and extending longitudinally within the shell 26 from a circular opening in the proximal end of the shell 26 to adjacent the distal end of the shell 26. In the illustrated embodiment, shaft-receiving cavity 46 has a diameter of approximately 0.375 inches.

The broach shell 26 includes a laterally opening slot 76 communicating with the shaft-receiving cavity 46 and extending through the side wall of the shell 26 adjacent the proximal end of the shell 26. A laterally opening channel 77 communicating with the shaft-receiving cavity 46 and the slot 76 extends through the side wall of the shell 26 below the slot 76. Channel 77 is wider than slot 76 to allow triangular broaches 34 to ride in the channel 77 but not in the slot 76. A triangular broach 34 riding straight upwardly in the channel 77 eventually engages a broach engaging wall 74 at the upper wall of channel 77 where the channel 77 and slot 76 form a junction. In the illustrated embodiment, slot 76 has a length 75 from the proximal end of the shell 26 to the wall 74. The length 75 of slot 76 facilitates insertion and removal of broach tools 22 from the shell 26 without requiring removal of the shell 26 from the bone 16, as described more fully below.

Broach shell 26 can include indicia 82 which relate to the geometry of the neck of the femoral prosthesis which is to be implanted. As shown in FIG. 1, these indicia are referenced to the most proximal portion 84 of the great trochanter 86 of the patient's femur 16. The index 82 which lines up with proximal portion 84 provides the surgeon with information regarding selecting the appropriate neck geometry for the femoral component. Additional notations can be included on broach shell 26 to indicate the sleeve cone sizes for which the broach shell 26 is appropriate (see reference numeral 88 in FIG. 1). A general reference number 90 to the cone size can also be imprinted on the broach shell 26.

The broach shells 26 and pilot stems 42 utilized with the present invention, are similar to miller shells and pilot stems utilized with triangular millers. Miller shells and pilot stems are disclosed in U.S. Pat. No. 5,540,694, which is incorporated herein by reference.

Figure 5:
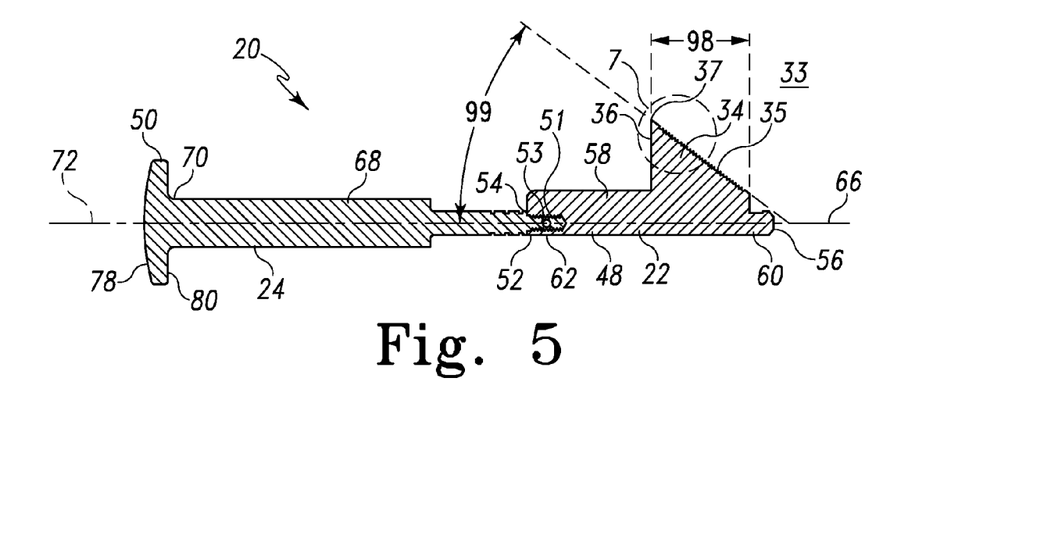
FIG. 5 is a sectional view taken along line 5-5 of FIG. 4 of the guided broach.
Figure 6:
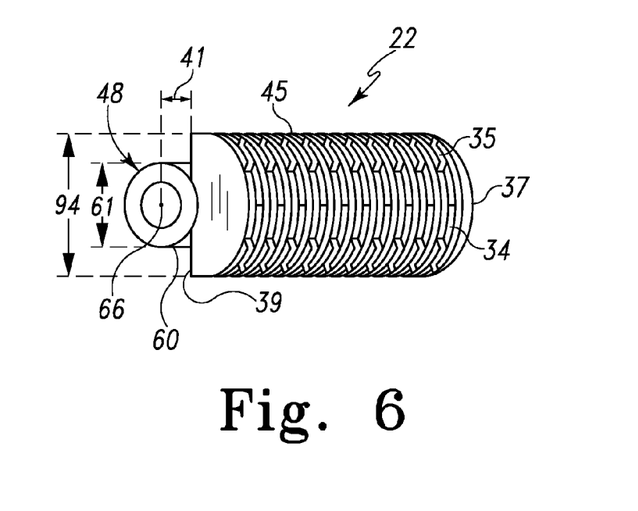
FIG. 6 is an end elevation view of the broach toll of the guided broach of FIG. 3.
Figure 7:
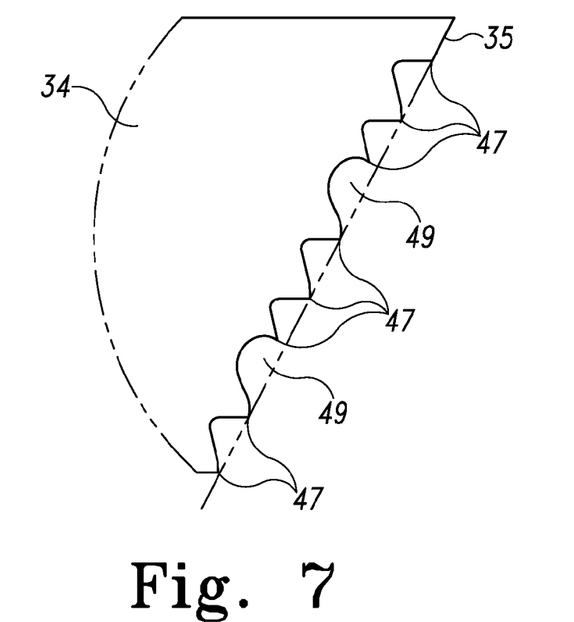
FIG. 7 is an enlarged view of the portion of the guided broach enclosed in phantom circle 7 in FIG. 5.

In the illustrated embodiment, broach tool 22 includes a shaft 48 having a longitudinal axis 66 and a triangular broach 34 extending laterally from the shaft 48. The proximal end 52 of the shaft 48 is configured to couple to the distal end 54 of the driver component 24. In the illustrated embodiment, as shown, for example, in FIG. 5, the distal end 54 of the driver component 24 is formed to include a threaded shaft 53 configured to be received in a threaded cavity 51 formed in the proximal end 52 of the shaft 48 of the broach tool 22. The distal end 56 of the shaft 48 is configured to be slidably received in the shaft-receiving cavity 46 of the broach shell 26. The shaft 48 includes an intermediate anti-rotation plate portion 58 disposed between a distal rod portion 60 and a proximal rod portion 62. The plate portion 58 is symmetrical about the plane of symmetry 33 of the triangular broach 34.

The longitudinal axis 66 of the shaft 48 of the broach tool 22, when the shaft 48 is received in the broach shell 26, as shown, for example, in FIG. 1, coincides with the longitudinal axis 40 of broach shell 26. Shaft 48 is sized to fit and slide longitudinally within shaft-receiving cavity 46 of broach shell 26. When shaft 48 is received in shaft-receiving cavity 46 of the broach shell 26, the anti-rotation plate 58 extends through the slot 76 formed in the upper portion of the broach shell 26 for longitudinal movement relative to the slot 76. To that end, anti-rotation plate 58 has a thickness 59 that is slightly less than the width 96 of the slot 76. In the illustrated embodiment, the thickness 59 of anti-rotation plate 58 is approximately 0.1965 inches while the width 96 of slot 76 is 0.1975 inches. Thus, the side walls of anti-rotation plate 58 and the walls forming slot 76 cooperate to guide the triangular broach 34 and prevent it from rotating while it is being driven through the bone 16 to form the triangular cavity 14.

Near the distal end 56 of shaft 48 the hypotenuse 35 of the triangular broach 34 is coupled to the shaft 48. The hypotenuse 35 of the triangular broach 34 forms an angle 99 with respect to the longitudinal axis 66 of the shaft 48. Angle 99 corresponds to the angle the projection, or spout, forms with the body of the sleeve of the prosthesis and the angle of the triangular cavity 14 to be formed in the bone. Illustratively, angle 99 is approximately thirty one and eighty-three hundredths degree) (31.83°).

Figure 11:
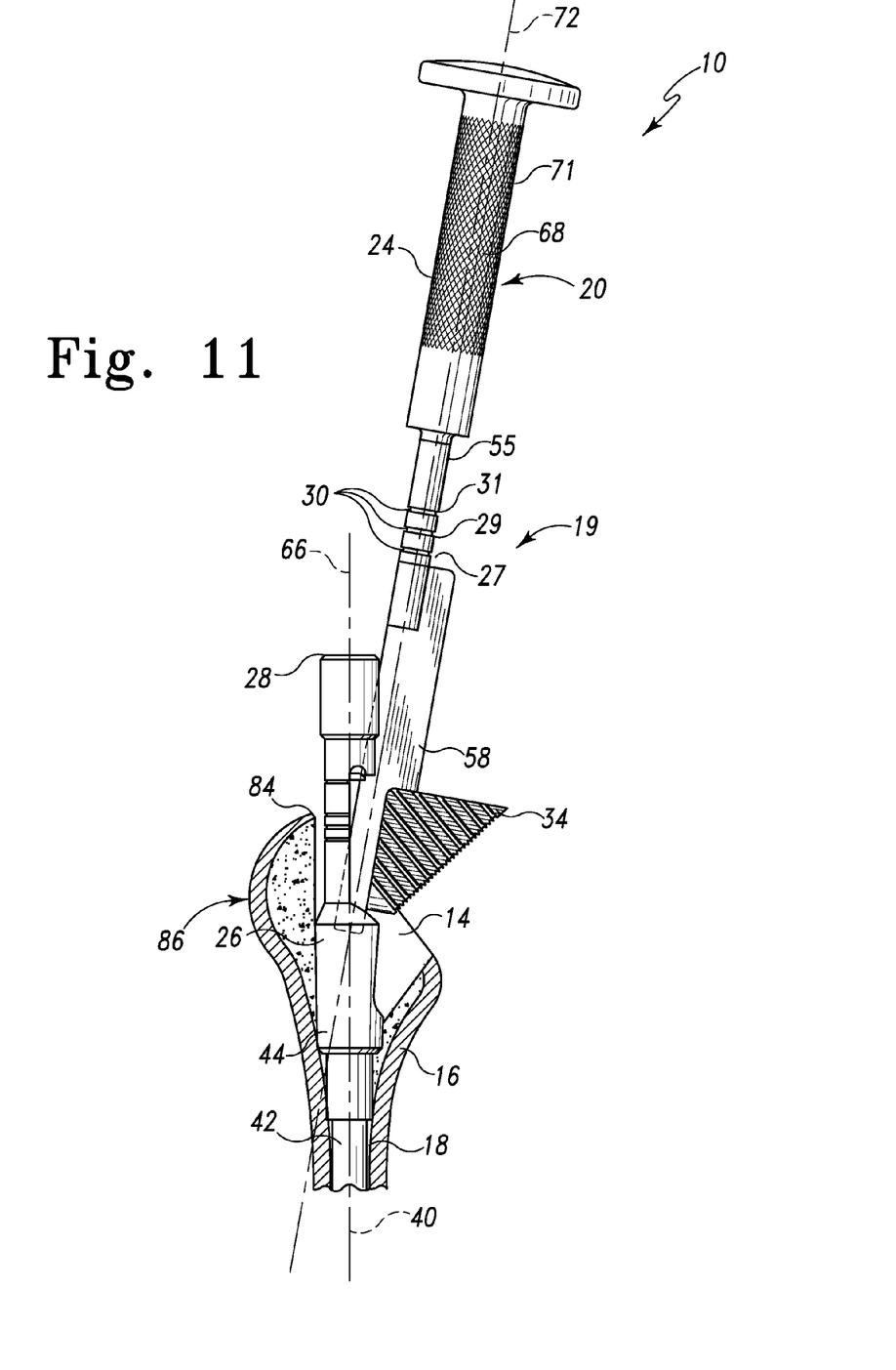

In the illustrated embodiments, the triangular broach 34 is configured as a right triangle having its hypotenuse side 35 extending at an acute angle 99 from adjacent the distal tip 56 of the shaft 48 upwardly and outwardly from the shaft 48. The upper surface 36 of the triangular broach 34 is generally perpendicular to the longitudinal axis 66 of the shaft 48. The upper surface 36 of the triangular broach 34 is displaced longitudinally from the distal end of the proximal rod portion 62 by a distance 43. In the illustrated embodiment, distance 43 is greater than the length 75 of slot 76 to facilitate insertion and removal of a broach tool 22 into the shell 26 without removal of the shell from the bone 16, as shown, for example, in FIG. 11. The side surface 39 of the triangular broach 34 is generally parallel to the longitudinal axis 66 and is displaced therefrom by a distance 41 approximately equal to the radius of the proximal rod portion 62 of the shaft 48.

At the corner 37 of the triangular broach 34 formed by the upper surface 36 and hypotenuse side 35, the broach tool 22 has a maximum width 32 (measured from the shaft 48 to the apex 37 of the triangular broach 34 perpendicular to the longitudinal axis 66 of the shaft 48). It is this maximum width 32 that dictates the minimal size of the incision 12 required to perform a prosthetic surgery. Thus, the surgical incision 12 required to use the disclosed guided broach 20 need only be large enough to allow retraction to a width only slightly larger than the maximum width 32 of the guided broach 20.

Figure 8:
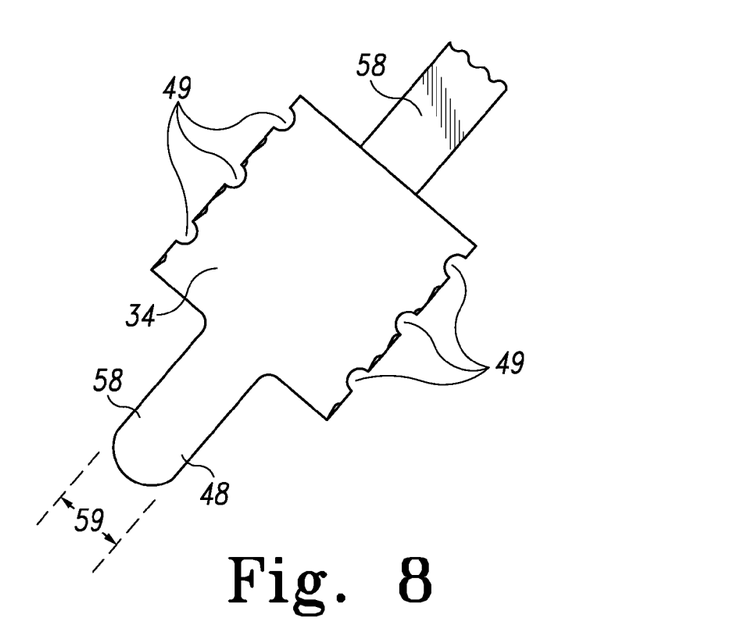
FIG. 8 is a sectional view taken along line 8-8 of the broach tool of FIG. 3.

Triangular broach 34 is formed symmetrically about a plane 33 including the longitudinal axis 66 of the shaft 48 of the broach tool 22. The hypotenuse wall 35 of the triangular broach 34 is curved to smoothly join with the oppositely facing side walls 45 of the triangular broach 34. The oppositely facing triangular shaped side walls 45 are generally parallel to the plane of symmetry 33 of the triangular broach 34. The triangular broach 34 is formed to include a plurality of rows of broach teeth 47 formed in the side walls 45 and hypotenuse wall 35. Illustratively, the each row of the plurality of rows of broach teeth 47 is formed in a plane perpendicular to the plane of symmetry 33 of the triangular broach 34 and the longitudinal axis 66 of the shaft 48 of the broach tool 22. A plurality of chip breakers 49 are formed in the side walls and hypotenuse wall 35 of the triangular broach 34. In the illustrated embodiment, each chip breaker 49 is a full rounded channel, as shown for example, in FIG. 8. In the side walls 45 each chip breaker 49 runs at an angle with respect to the top surface 36 of the triangular broach 34. Illustratively, the chip breaker angle is approximately forty-five degrees.

The disclosed plurality of broach tools 22 include differently sized triangular broaches 34 coupled to the shaft 48 to allow calcar preparation of the femur for receipt of prosthesis having differently sized sleeves or projections from the stem component. Illustratively, broach tools 22 for calcar preparation of a femur for receipt of sleeves of the S-ROM modular prosthesis which includes a plurality of differently sized sleeves have maximum widths 32 of approximately 1.789 inches. For example, seven differently sized broach tools 22 designated 7×12, 9×14, 11×16, 13×18, 15×20, 17×22 and 19×24, respectively, are provided for use with the S-ROM modular prosthesis system. In such broach tools 22, the thickness 94 of the triangular broach 34 varies depending on the size of triangular cavity 14 to be prepared. The triangle broaches 34 of broach tools 22 for utilization with the S-ROM modular prosthesis system for example have thicknesses 94 of approximately 0.315, 0.394, 0.472, 0.551, 0.630, 0.709, and 0.787 inches, respectively, to accommodate the plurality of differently sized sleeves provided in such modular prosthesis system. In such broach tools 22, the length 98 of the triangular broach 34 varies depending on the size of triangular cavity 14 to be prepared. The triangle broaches 34 of broach tools 22 for utilization with the S-ROM modular prosthesis system for example have lengths 98 of approximately 1.780, 1.780, 1.780, 1.780, 1.820, 1.880, and 1.880 inches, respectively, to accommodate the plurality of differently sized sleeves provided in such modular prosthesis system.

The driver component 24 includes a strike plate 50 coupled to a shaft 68. Shaft 68 includes a proximal end 70, a distal end 54 and a longitudinal axis 72. The strike plate 50 is coupled to the proximal end 70 of shaft 68 as shown, for example, in FIGS. 1-5. In the illustrated embodiment, the shaft 68 includes a proximal portion 71 adjacent the proximal end 70 that is a larger diameter than the distal portion 55 adjacent the distal end 54. The proximal portion 71 is knurled to facilitate gripping the shaft 68 as it is being used to drive the guided broach 20 into the bone 16. In the illustrated embodiment, the proximal portion 71 of the shaft 68 terminates at a location that would not require insertion of the proximal portion 71 into the incision 12 during the surgical operation.

The distal portion 55 of the shaft 68 may be partially inserted into the incision 12 during the surgical procedure and portions of the distal portion 55 may even be received in the shaft-receiving cavity 46 of the broach shell 26. Thus, the distal portion 55 of the shaft 68 has a diameter 57 approximately equal to the diameter 63 of the proximal rod portion 62 and the diameter 61 of the distal rod portion 60 of the shaft 48 of the broach tool 22. In the illustrated embodiment, diameters 57, 61 and 63 are approximately 0.372 inches to facilitate receipt of the distal portion 55 of the shaft 68 and the proximal rod portion 62 and distal rod portion 60 of the shaft 48 of the broach tool 22 in the shaft-receiving cavity 46 of the broach shell 26 for longitudinal movement of the guided broach 20 relative to the shell 26.

The distal portion 55 of the illustrated shaft 68 is formed to include witness marks 30. The witness marks 30 are utilized in the same manner as witness marks are utilized in currently available triangle milling devices. For example, in the illustrated embodiment, three witness marks 30 are provided on the distal portion 55 of the shaft 68 corresponding to three differently sized sleeves available in the modular prosthesis (small, large and double extra large). The small sleeve witness mark 27 is located closest to the distal end 54 of the shaft 68 with the large sleeve witness mark 29 disposed between the double extra large witness mark 31 and the small sleeve witness mark 27.

When the triangular broach 34 contacts bone 16 during calcar preparation, broaching is stopped if a witness mark 30 is currently adjacent an indicator mark 28 (illustratively the proximal end of the broach shell 26) and the sleeve corresponding to that witness mark 30 is utilized during prosthesis installation. Otherwise, broaching is continued to remove enough of the bone 16 to bring the next witness mark 30 adjacent the indicator mark 28 and the sleeve corresponding to that witness mark is utilized during prosthesis installation.

Thus, if for example, a surgeon through pre-surgical analysis determines that a small sleeve of a modular prosthesis system, should be utilized in the prosthesis, the surgeon would initially drive the guided broach 20 into the bone 16 until the small sleeve witness mark 27 is adjacent the indicator mark 28 on the shell 26. If at this time, the broach 34 has contacted bone 16 of the appropriate consistency, broaching would be stopped and the small sleeve would be utilized with the modular prosthesis. If bone has not been contacted by the triangular broach 34 or the contacted bone is not of the appropriate consistency, broaching would be continued until the large sleeve indicator mark 29 is adjacent the indicator mark 28 on the shell 26. If at this time, the broach 34 has contacted bone 16 of the appropriate consistency, broaching would be stopped and the large sleeve would be utilized with the modular prosthesis. If at that time bone has not been contacted by the triangular broach 34 or the contacted bone is not of the appropriate consistency, broaching would be continued until the double extra large sleeve indicator mark 31 is adjacent the indicator mark 28 on the shell 26 and the double extra large sleeve would be utilized with the modular prosthesis.

As discussed above, broach tool 22 and broach shell 26 include indicators 28, 30. The illustrated indicators or witness marks 30 comprise three indices 27, 29, 31 corresponding to three different triangles, referred to as small ("SML"), large ("LRG"), and double extra large ("XXL") in the figures. More or less indices can be used as desired and, of course, can be otherwise designated. Illustratively, indicator 28 comprises the upper end of broach shell 26. However, it is within the scope of the disclosure for broach shell 26 to include other structures or indicia thereon acting as indicator 28 for alignment with indicators 30 of guided broach 20.

Those skilled in the art will recognize that the position of the witness marks 30 may be varied to permit the witness marks to be aligned with other indicia of the appropriate size of sleeve to be selected. For instance, the witness marks may be positioned along the shaft 48 of the broach tool 22 to align with indicia on the broach shell 26, witness marks may be provided on the broach tool 22 that align with indicia on the broach shell 26 or witness marks may be provided on the broach shell 26 that align with indicia on the broach tool 22. It is within the scope of the disclosure for other indicia to be provided from which the surgeon can determine when to stop broaching the bone and from which the surgeon can determine the appropriate sleeve to select from a modular prosthesis system.

The strike plate 50 is a rounded circular plate including a top surface 78 configured to be struck by a mallet and a planar bottom surface 80 substantially perpendicular to the longitudinal axis 72 of the driver 24. In the illustrated embodiment, shaft 68 is welded to strike plate 50. The top surface 78 of the strike plate 50 facilitates exerting downward pressure on the guided broach 20 during the broaching process. The strike plate 50 can also be used to remove the broach tool 22. Removal of the broaching system 10 from the bone cavity may be accomplished by striking the bottom surface 80 of the strike plate 50 with a mallet. The strike plate 50 also facilitates extraction of the broach tool 22, broach shell 26 and pilot stem 42 following bone cutting (see below).

As mentioned previously triangular broach 34 has a thickness 94 that is greater than the width of the slot 76. Illustratively, thickness 94 of triangular broach 34 is equal to or exceeds approximately 0.315 inches. Thus, when the guided broach is slid upwardly within the broach shell 26, the triangular broach 34 cannot fit within slot 76. Therefore, the top surface 36 of the triangular broach engages broach engagement surface 74 adjacent the distal opening of slot 76 during upward movement of the guided broach 20. The engagement of top surface 36 of the triangular broach 34 with broach engagement surface 74 transfers removal forces applied to the guided broach 20 to the broach shell 26 facilitating removal of the broach shell 26 and the pilot stem 42 coupled thereto from the bone 16.

Referring now to FIG. 1 there is shown a broach assembly 19 formed from a broach shell 26, a broach tool 22, a pilot stem 42 and a driver component 24 of the broaching system 10. The broach tool 22 is slidably received in the broach shell 26 for reciprocal movement along the longitudinal axis 40 of the broach shell 26. The pilot stem 42 is received in a previously reamed cylindrical cavity. Pilot stem 42 is coupled to broach shell 26 to align the axis 40 of broach shell 26 relative to the cylindrical cavity. The frustoconical surface 44 of the broach shell 26 is received in the previously reamed conical cavity. The pilot stem 42 and broach shell 26 are selected from the plurality of pilot stems 42 and broach shells 26 based on the size of the reamers used to form the cylindrical and conical cavities, respectively.

As shown, for example, in FIGS. 1-6, the broach tool 22 includes a distal rod portion 60 and proximal rod portion 62 coupled to the anti-rotation plate 58 to which the triangular broach 34 is coupled. Anti-rotation plate 58 and the distal portion 60 and proximal portion 62 of the shaft 48, are all aligned as shown, for example, in FIG. 4, so that they slide within the shaft-receiving cavity 46 and slot 76 formed in broach shell 26. Anti-rotation plate 58 engages the walls of the laterally opening slot 76 in broach shell 26 to prevent rotation of the triangular broach 34 with respect to the shell 26 during calcar preparation. As the broach tool 22 is reciprocated upwardly (proximally) within the broach shell 26, the top surface 36 of the triangular broach 34 comes into engagement with the broach engagement surface 74 adjacent the distal end of the slot 76 in the broach shell 26. Thus, removal of the broach tool 22 from the calcar cavity induces the broach shell 26 and pilot stem 42 to be removed from the straight and conically reamed cavities in the intramedullary canal 18.

During assembly of a broach assembly 19 from components of the broaching system 10, an appropriately sized broach shell 26 is selected and an appropriately sized pilot stem 42 is coupled to the distal end of the broach shell 26. The broach shell 26 and pilot stem 42 are selected based on the size of the straight and conical reamers used to prepare the intramedullary canal 18. The driver component 24 is coupled to the broach tool 22 which is assembled into broach shell 26. Illustratively, a threaded shaft 53 extends from the distal end 54 of the driver component 24 that is configured to be received in a threaded cavity 51 formed in the proximal end 52 of the broach tool 22.

As shown, representatively by two broach tools 22 in FIG. 2, a family of broach tools 22 is preferably provided to the surgeon with all members of the family having commonly sized shafts 48 to permit assembly of any on of the broach tools 22 with any one of the broach shells 26. Each broach tool 22 of the family also includes a commonly sized threaded cavity 51 to facilitate assembling any broach tool 22 of the family to the driver component 24 to form a guided broach 20.

The broach tool 22 and broach shell 26 are configured so that the guided broach 20 may be inserted and removed from a broach shell 26 seated in the prepared cavities of the bone 16. As shown, for example, in FIG. 11, the longitudinal axis 66 of the broach tool 22 may be tilted at an angle with respect to the axis 40 of the broach shell and the distal rod portion 60 of the shaft 48 may be inserted through the channel 77 into the shaft-receiving cavity 46. The anti-rotation plate 58 of the broach tool 22 may be slid into the slot 76 in the broach shell 26 while the upper surface 36 of the triangular broach 34 is disposed below the broach engagement surface 74 and the distal end of the proximal rod portion 62 of the shaft is disposed above the proximal end of the broach shell 26. The guided broach 20 may then be tilted to align the longitudinal axes 66, 72 of the broach tool 22 and driver component 24, respectively, with the longitudinal axis 40 of the broach shell 26. Once the axes 66, 72 and 40 are aligned, the guided broach 20 may be reciprocated longitudinally with respect to the broach shell 26 with the proximal rod portion 62 of the shaft 48 of the broach tool 22 and portions of the distal portion 55 of the driver component 24 being received in the shaft-receiving cavity of the shell 26. Removal of the guided broach 20 from the broach shell 26 is accomplished in the opposite fashion when it is desired to remove the guided broach 20 from the broach shell 26 while leaving the broach shell seated in the bone 16.

Figure 9:
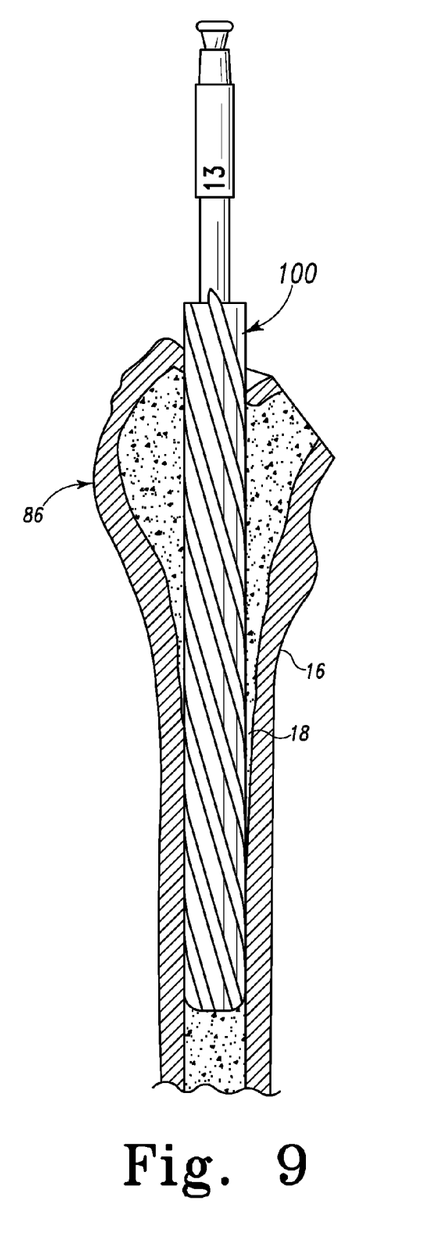
FIG. 9 is a view with surrounding skin and tissue removed of a patient's resected a femur with parts broken away showing the final straight reamer used to prepare the intramedullary canal for a prosthesis.

The overall procedure in which broaching system 10 is used is similar in most steps to those described in greater detail in the Background of the Invention. Generally, an incision 12 large enough to receive the maximum width 32 of the broach tool 22 is made through which the patient's femur 16 is prepared. The head of the femur 16 is resected using an osteotome, oscillating saw or other instrument. An osteotome may be utilized to open the femoral canal 18. The femoral canal 18 is then reamed with a straight reamer 100 to establish an extended cavity and center line for receipt of the distal stem of the femoral prosthesis and the pilot stem 42 of the broaching system 10, as shown, for example, in FIG. 9. As described in the Background and Summary, the straight reaming step may be accomplished utilizing a plurality of straight reaming steps in which reamers 100 having progressively larger diameters are utilized.

Figure 10:
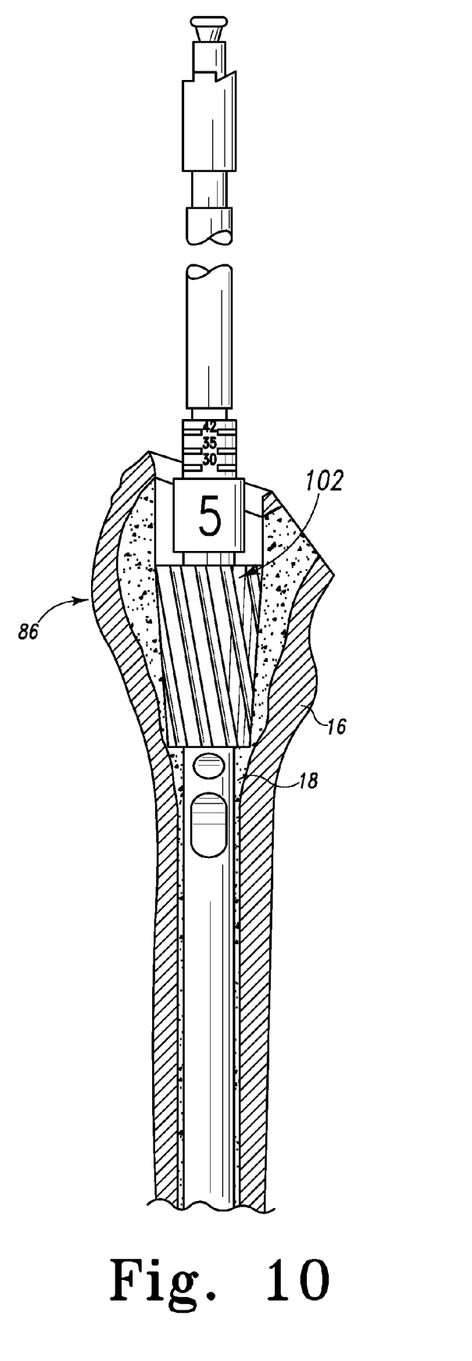
FIG. 10 is a view similar to FIG. 9 showing the final conical reamer used to prepare a conical cavity in the intramedullary canal for a prosthesis; and, FIG. 11 is a view similar to FIG. 10 showing a broach assembly including a broach shell and a pilot stem inserted in the straight and conical cavities formed in the femur and a guided broach positioned for insertion into or removal from the broach shell.

Next, the intramedullary canal 18 of the proximal femur 16 is reamed with conical reamers 102 to form a cavity for receiving the conical portion of a sleeve or a stem of a prosthesis and the frustoconical portion 44 of the broach shell 26 of the broaching system 10, as shown, for example, in FIG. 10. This conical cavity is on the same center line as the straight cavity and the reaming is conducted until the proximal end of the reamer 102 is even with the proximal end of the resected femur. As described in the Background and Summary, the conical reaming step may be accomplished utilizing a plurality of conical reaming steps in which conical reamers 102 having progressively larger maximum and minimum diameters are utilized.

Components of the broaching system 10 in its assembled form are shown in FIG. 1 inserted into the proximal end of the femur 16. The assembled instrument, or broach assembly 19, includes a guided broach 20, broach shell 26 and a pilot stem 42. The guided broach includes a broach tool 22 and a driver component 24. The broach tool 22, broach shell 26 and pilot stem 42 are appropriate to 1) the size of the triangular projection of the sleeve which the surgeon wishes to implant, and 2) fit within the straight and conical cavities formed in the bone. As described below, this calcar preparation step may be performed using a single guided broach 20 or a plurality of guided broaches 20 having triangular broaches 34 with progressively increasing thicknesses 94.

Specifically, the broach assembly 19 is selected based on the width W of the triangular projection (or spout) of the sleeve which is to be implanted (see FIG. 1 of incorporated U.S. Pat. No. 5,540,694). The broach shell 26 is selected based on the size of the conical reamer used in step 2. Specifically, frustoconical portion 44 of broach shell 26 has the same taper and same maximum diameter as the conical reamer. The height of frustoconical portion 44 is preferably slightly less than the height of the conical reamer so that the proximal end of the frustoconical portion 44 can be aligned with the resected end of the femur 16 without bottoming out in the reamed conical cavity. The pilot stem 42 is selected based on the size of the final straight reamer used in step 1 which in turn is selected by the surgeon based on the inside diameter of the patient's femur 16.

To provide the surgeon with the ability to match the finished prosthesis to various patient requirements, sleeves of various sizes and configurations and femoral prostheses having various proximal and distal diameters are provided to the surgeon along with corresponding sets of guided broaches 20, pilot stems 42, broach shells 26, straight reamers and conical reamers. Guided broaches 20 may comprise a plurality of integrally formed broach tools 22 and driver components 24 or a plurality of broach tools 22 and a single driver component 24 configured to mate with each of the plurality of broach tools 22 within the scope of the disclosure.

The initial insertion of broach assembly 19 into the cavity in the femur brings the proximal end of frustoconical portion 44 into alignment with the proximal end of the resected femur 16. At this point, the surgeon can use indicia 82 to confirm his or her selection of a neck geometry for the femoral prosthesis. Calcar broaching is accomplished using an appropriately sized pilot stem 42 for the distally reamed canal, an appropriately sized broach shell 26 for the size of the cone milling performed and a guided broach 20. In the illustrated embodiment, the threaded proximal end of the pilot stem 42 is screwed into a threaded aperture in the distal end of the broach shell 26. The pilot stem 42 is inserted into the reamed canal 18 until the frustoconical portion 44 of the shell 26 is seated in the conical aperture created during cone milling. The guided broach 20 is configured to be slidably received in the shell 26. Once the broach 20 is partially inserted into the shell 26, the assembly 19 is rotated to position the triangular broach 34 of the broach tool 22 over the best available host bone, which may or may not be in the calcar.

The guided broach 20 is then lowered until the triangular broach 34 of the broach tool 22 makes contact with the cancellous bone. Once in contact with the cancellous bone, a hammer is used to strike the strike plate 50 on the proximal end of the guided broach 20 to drive the triangular broach 34 of the broach tool 22 into the femur until the cortical bone is contacted. Once the cortical bone is contacted, the surgeon examines the witness marks 30 on the shaft 68 of the broach 20 to determine which mark is most closely aligned with the proximal end of the shell 26. In one embodiment of a method of calcar preparation, three increasingly larger guided broaches 20 are utilized to create the triangular calcar cavity.

Triangular broach 34 is then driven into the bone 16 by impacting the driver component 24 with an appropriate instrument or tool, such as a mallet, while broach tool 22 is moved along longitudinal axis 40 of broach shell 26. This process is continued until the appropriate index 30 on broach tool 22 is aligned with reference surface 28, e.g., until the "LRG" index 29 is aligned if the sleeve to be inserted is to have a "LRG" triangular projection. In some cases, the original choice of triangular projection may be too small to reach the patient's hard calcar bone at the proximal end of the femur 16, in which case the cutting of the triangular cavity 14 would be continued to the next index mark 30 and a further evaluation would be made at that point. If suitable at this point, a sleeve having a triangular projection portion or spout corresponding to the index mark 30 to which the cutting was continued would be used. Depending upon the circumstances, all or portions of the process may be repeated until a suitable fit is achieved.

The broach assembly 19 is removed from the patient's femur by pulling guided broach 20 straight out using the strike plate 50 of the driver component 24. During removal the top surface 36 of the triangular broach 34 engages with surface 74 of broach shell 26. A light tap on the strike plate 50 from below with a hand, mallet, or other instrument, is usually sufficient to release broach shell 26 from the patient's bone allowing complete removal of the broach assembly 19. Implantation of the femoral prosthesis then follows.

In one embodiment of a method of broaching the triangular cavity 14 in a bone 16, guided broaches 20 having triangular broaches 34 with progressively wider thicknesses 94 are utilized sequentially to form the triangular cavity 14. As described above, in one embodiment of the broaching system 10 for use in preparation of a bone for receipt of an S-ROM modular prosthesis, seven broach tools are provided designated sizes 7×12, 9×14, 11×16, 13×18, 15×20, 17×22 and 19×24. These sizes correspond to the sizes of sleeves available in the modular prosthesis system. Thus, if the surgeon intends to utilize a size 13×18 sleeve, the initial guided broach 20 selected for calcar preparation would include the size 9×14 broach tool 22. After broaching the triangular cavity 14 to the appropriate depth using the 9×14 broach tool 22, the guided broach 20 would be removed from the broach shell 26 and the 9×14 broach tool 22 would be replaced with the 11×16 broach tool 22. The guided broach 20 including the 11×16 broach tool 22 would then be inserted into the broach shell 26 and driven into the bone 16 to the appropriate depth. The guided broach 20 would then again be removed from the broach shell 26 and the 11×16 broach tool 22 would be replaced with the 13×18 broach tool 22. The guided broach 20 including the 13×18 broach tool 22 would then be inserted into the broach shell 26 and driven into the bone 16 to the appropriate depth. The guided broach 20 would then be pulled straight up until the top surface 36 of the triangular broach 34 engages the broach engagement surface 74 of the broach shell 26 and the guided broach 20, broach shell 26 and pilot stem 42 would be removed from the femur 16.

Broaching system 10 is fabricated using conventional techniques used in the manufacture of surgical instruments. Similarly, the broaching system 10, is composed of conventional stainless steels or other materials employed in constructing surgical instruments.

Although specific embodiments of the invention have been described herein, other embodiments may be perceived by those skilled in the art without departing from the scope of the invention as defined by the following claims. For example, although the invention has been described in terms of the implantation of the femoral portion of a hip prosthesis, it can be used with prostheses for other joints such as the shoulder, knee, or elbow.

What is claimed is:

1. A device for creating a cavity in a bone, said cavity (i) having a cross section which has a generally triangular profile having a first side generally parallel with an axis of the bone and a second side forming an acute angle with the first side, and (ii) contiguous with a pre-existing conical cavity in the bone, said device comprising:
   a shaft having a longitudinal axis and including a proximal portion and a distal portion, wherein the proximal portion has a larger cross section perpendicular to the longitudinal axis than the corresponding cross section of the distal portion; and
   a broach non-rotationally supported by the shaft and having a first cutting side supported at the acute angle relative to the longitudinal axis of the shaft, wherein the distal portion of the shaft is formed to include witness marks which when registered with an indicator after advancing the shaft facilitate selection of an appropriately sized prosthesis component.

2. The device of claim 1 wherein the broach is supported adjacent the distal portion and further comprising a driver coupled to the proximal portion.

3. The device of claim 1 wherein the broach includes oppositely facing spaced apart triangular shaped side walls between which the first cutting side extends.

4. The device of claim 1 wherein the distal portion is removably attached to the proximal portion.

5. The device of claim 1 and further comprising a broach shell configured to register the device with the pre-existing conical cavity, the broach shell having a broach longitudinal axis, an external surface with a portion configured to engage the wall of the pre-existing conical cavity, and a cavity configured to receive the shaft and allow the shaft to move along the broach longitudinal axis when the shaft is received within the cavity.

6. The device of claim 5 and wherein the broach shell includes indicia related to a geometry of a neck of a femoral prosthesis.

7. A kit for creating a cavity in a bone for receiving a prosthesis which has a conical portion and a projection of a generally triangular profile, said kit comprising:
   a first shell comprising a conical portion which defines a longitudinal axis and a shaft-receiving cavity for receiving a shaft;
   a first shaft configured to be received in the shaft-receiving cavity and movable with respect to the first shell along the longitudinal axis when so received; and
   a first broach having a generally triangular profile and including oppositely facing spaced apart generally triangular shaped side walls between which a first cutting surface extends, the first broach mounted to the first shaft such that the first cutting surface is disposed at an acute angle relative to the longitudinal axis.

8. The kit of claim 7 wherein:
   the first shell includes a longitudinal slot communicating with the shaft receiving cavity through a wall of the first shell;
   the first shaft includes a plate configured to be received in the slot for longitudinal movement relative to the slot when the first shaft is received in the shaft-receiving cavity, the longitudinal slot and the plate cooperating to inhibit rotation of the first shaft about the longitudinal axis.

9. The kit of claim 7 and further comprising a driver component coupled to the first shaft.

10. The kit of claim 9 wherein the driver component is removably coupled to the first shaft and further comprising:
    a second shaft configured to be received by the shaft-receiving cavity and movable with respect to the first shell along the longitudinal axis when so received, said shaft configured to be removably coupled to the driver component; and
    a second broach having a generally triangular profile and including oppositely facing spaced apart generally triangular shaped side walls between which a second cutting surface extends, the side walls spaced apart by a displacement greater than the displacement between the side walls of the first broach, the second broach mounted to the second shaft.

11. The kit of claim 10 and further comprising a second shell comprising a conical portion which defines a longitudinal axis and a shaft-receiving cavity configured to receive either of the first and second shaft wherein the conical portion of the second shell is larger than the conical portion of the first shell.

12. The kit of claim 11 and further comprising a first pilot stem configured for removable coupling to either of the first and second shell and having a first diameter sized to be received in a first cavity formed in the intramedullary canal of the bone, and a second pilot stem configured for removable coupling to either of the first and second shell and having a second diameter, the second diameter smaller than the first diameter.

13. The kit of claim 12 wherein:
    the first and second shell each include a respective longitudinal slot communicating with the respective shaft receiving cavity through a wall of the respective shell; and the first and second shaft are each formed to include a respective plate configured to be received in the respective longitudinal slots for longitudinal movement relative to the respective longitudinal slots when the first and second shaft is received in the respective shaft-receiving cavity of the first or second shell, the respective longitudinal slot and the respective plate cooperating to inhibit rotation of the first and second shaft about the longitudinal axis.

14. The kit of claim 13 wherein;
the first and second shell each include a respective longitudinal channel communicating with the respective shaft receiving cavity through a respective wall of the first and second shell and communicating with the respective longitudinal slot, the respective longitudinal channel configured to allow the first and second broach to travel uninhibited therein as the first and second shaft are advanced distally within the respective shaft receiving cavity.

15. The device of claim 1, further comprising:

a second cutting side supported by the shaft; and a third cutting side supported by the shaft, wherein the first cutting side extends between the second cutting side and the third cutting side.

16. The device of claim of claim 1, further comprising a shell including:

a cavity configured to slidingly receive the shaft; and a channel extending from the cavity to an outer wall of the shell, the shell configured such that when the shaft is slidingly received within the cavity, a plate fixedly attached to the shaft extends within the channel such that the shaft can move along the cavity but cannot rotate within the cavity.

* * * * *